United States Patent [19]

Russell et al.

[11] Patent Number: 5,208,252

[45] Date of Patent: May 4, 1993

[54] AMINOETHYLTHIOPHENE DERIVATIVES

[75] Inventors: Ronald K. Russell, Titusville, N.J.; Joseph J. Salata, Newtown, Pa.

[73] Assignee: Ortho Pharmaceutical Corporation, Raritan, N.J.

[21] Appl. No.: 919,650

[22] Filed: Jul. 24, 1992

[51] Int. Cl.$^5$ .................. A61K 31/38; C07D 333/20
[52] U.S. Cl. ......................... 514/438; 549/74; 549/75; 549/77; 514/821
[58] Field of Search .................. 549/77, 75, 74; 514/438, 821

[56] References Cited

U.S. PATENT DOCUMENTS

| | | | |
|---|---|---|---|
| 4,128,561 | 12/1978 | Braye | 549/74 |
| 4,460,580 | 7/1984 | Ostermayer et al. | 549/77 |
| 5,117,000 | 5/1992 | Suzuki et al. | 549/77 |

OTHER PUBLICATIONS

R. T. Gilsdorf et al., *Journal of Organic Chemistry*, 15 pp. 807–811 (1950).
S. Conde et al., *Journal of Medicinal Chemistry*, 21 (9), pp. 978–981 (1978).
J. Arrowsmith et al., in "Annual Reports in Medicinal Chemistry" J. Bristol ed., vol. 25, pp. 79–88, Academic Press, Inc., New York (1990).
M. Steinberg et al., in "Annual Reports in Medicinal Chemistry," vol. 21, pp. 95–108, Academic Press, Inc., New York (1986).

*Primary Examiner*—Glennon H. Hollrah
*Assistant Examiner*—Mark W. Russell
*Attorney, Agent, or Firm*—Joseph J. Brindisi

[57] ABSTRACT

This invention relates to aminoethylthiophene derivatives and more particularly 2-and 3-aminoethylthiophene derivatives which are useful as antiarrhythmic agents, their methods of use as antiarrhythmic agents, and novel intermediate compounds useful for preparation of the aminoethylthiophene derivatives of the invention.

14 Claims, No Drawings

AMINOETHYLTHIOPHENE DERIVATIVES

FIELD OF THE INVENTION

This invention relates to aminoethylthiophene derivatives and more particularly 2-and 3-aminoethylthiophene derivatives which are useful as antiarrhythmic agents.

BACKGROUND OF THE INVENTION

It has been estimated that in persons between the ages of 35 and 64 years of age, nearly 1 death in three is due to coronary heart disease [Gordon, T.; Kannel, W. B. *J. Amer. Med. Assoc.*, 1971, 215, 1617] and there are approximately 400,000 sudden cardiac deaths annually in the United States alone [Green, H. L.; et al., *Amer. J. Cardiology*, 1989, 63, 1]. During the last few years, development of drugs to treat cardiac arrhythmias (sudden cardiac death) has received much attention [Steinberg, M. I.; Lacefield, W. B.; Robertson, D. W. Class I and III Antiarrhythmic Drugs. In *Ann. Reports in Med. Chem.*, Bailey, D. M., Ed.; Academic Press, Inc.: Orlando, 1986; 21, pp 95–108; Arrowshmith, J. E.; Cross, P. E. Antiarrhythmic Agents. In *Ann Reports in Med. Chem.*, Bristol, J. A., Ed.; Academic Press, Inc.: San Diego, 1990; 25, pp 79–88]. A classification scheme of antiarrhythmic drugs has been presented by Vaughan Williams [Vaughan Williams, E. M. *J. Clin. Pharmacol.*, 1984, 24, 129] which is based on their electrophysiological effects on cardiac tissue.

Class I agents and subclasses (Ia, Ib, Ic) are defined as antiarrhythmic agents which have inhibitory effects on the sodium channel which result in a reduction of conduction velocity in the cardiac tissue. The class I agents are currently the most widely used for antiarrhythmic therapy. Recent results of the Cardiac Arrhythmia Suppression Trial (CAST) [*N. Engl. J. Med.*, 1989, 321, 406] have raised concerns about the Class IC subtype (e.g. flecainide) and suggest that antiarrhythmic drugs having other mechanisms of action should be considered.

Specific Class III antiarrhythmic drugs (e.g. d-sotalol) do not affect cardiac sodium channels or conduction velocity. These agents selectively prolong the cardiac action potential duration and thereby increase the effective refractory period (ERP). Prolongation of refractoriness is an effective means of preventing or terminating atrial and ventricular arrhythmias, the latter of which can be life threatening.

The discovery and development of new Class III antiarrhythmic agents which may be effective for reducing arrhythmias is desirable and is an object of the present invention.

It is therefore an object of the invention to provide novel compounds which are useful as antiarrhythmic agents. Additional objects and advantages of the invention will be set forth, in part, in the description which follows and in part will be obvious from this description, or may be learned by practice of the invention. The objects and advantages of the invention are realized and obtained by means of the compounds and methods particularly pointed out in the appended claims.

SUMMARY OF THE INVENTION

To achieve the object in accordance with the purposes of the invention, as embodied and fully described herein, the invention comprises novel compounds which are 2- and 3-aminoethylthiophene derivatives of the formula:

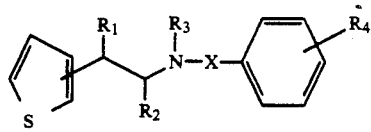

where $R_1$ and $R_2$ are the same or different and are hydrogen, $C_1$–$C_4$ alkyl, $C_3$–$C_5$ branched chain alkyl, aryl, preferably phenyl or aralkyl preferably substituted phenyl wherein the substituents are halogen, $C_1$–$C_6$ alkyl or $C_1$–$C_6$ alkoxy;

$R_3$ is hydrogen, $C_1$–$C_6$ alkyl or $C_3$–$C_5$ branched chain alkyl;

X is $(CH_2)_n$, $(CH_2)_{n+1}O$, $(CH_2)_2NR_5CO$, or $(CH_2)_2NR_5SO_2$;

$R_4$ is a mono-, di- or tri- substituent which may be the same or different and is halogen, $NO_2$, $NH_2$, $NHCOR_6$ or $NHSO_2R_6$;

n is 1–5;

$R_5$ is hydrogen, $C_1$–$C_4$ alkyl or $C_3$–$C_5$ branched chain alkyl; and $R_6$ is $C_1$–$C_4$ alkyl, $C_3$–$C_5$ branched chain alkyl or phenyl.

In preferred embodiments of the compounds of the invention $R_1$ and $R_2$ are hydrogen or $C_1$–$C_3$ alkyl; $R_3$ is hydrogen or $C_1$–$C_5$ alkyl; $R_4$ is $NO_2$ or $NHSO_2R_6$; n is 2–4; $R_5$ is hydrogen; and $R_6$ is methyl.

The present invention also includes substantially pure sterochemical isomers and pharmaceutically acceptable salts of the above-described compounds.

The compounds of the above formula are useful as antiarrhythmic agents, i.e. agents that increase the effective refractory period (ERP) and may serve to reduce the incidents of arrhythmias and thereby reduce the incidents of sudden cardiac death.

As embodied and fully described herein, the invention further comprises a method of increasing the ERP in a patient and reducing the incidents of arrhythmias comprising the step of administering an ERP increasing effective amount of an aminoethylthiophene derivative as described above to a patient in danger of suffering cardiac arrhythmias.

As embodied and fully described herein, the invention further comprises novel intermediate compounds for preparing the 2- and 3-aminoethylthiophene derivatives described above. These novel intermediate compounds have the formula:

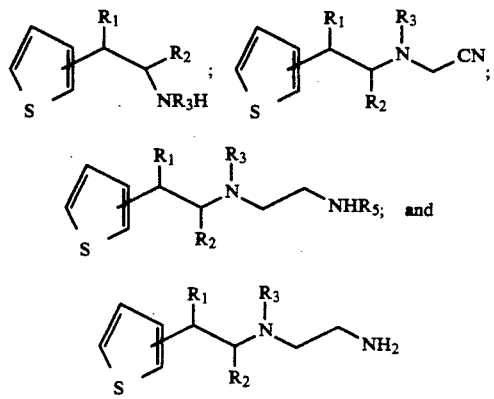

where
- $R_1$ and $R_2$ are the same or different and are hydrogen, $C_1$-$C_4$ alkyl, $C_3$-$C_5$ branched chain alkyl, aryl, preferably phenyl or aralkyl preferably substituted phenyl wherein the substituents are halogen, $C_1$-$C_6$ alkyl or $C_1$-$C_6$ alkoxy;
- $R_3$ is hydrogen, $C_1$-$C_6$ alkyl or $C_3$-$C_5$ branched chain alkyl;
- X is $(CH_2)_n$, $(CH_2)_{n+1}O$, $(CH_2)_2NR_5CO$, or $(CH_2)_2NR_5SO_2$;
- n is 1-5; and
- $R_5$ is hydrogen, $C_1$-$C_4$ alkyl or $C_3$-$C_5$ branched chain alkyl.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention; examples of which are illustrated in the following examples section.

In accordance with the invention novel compounds, compositions and methods are provided to achieve the objects in accordance with the purposes of the invention, as embodied and fully described herein. The invention provides novel 2-aminoethylthiophene and 3-aminoethylthiophene compounds of the above described formula which have been demonstrated to increase the effective refractory period (ERP) of isolated superfused cardiac tissue in vitro.

Compounds of the above formula can be prepared according to the reaction Scheme outlined below.

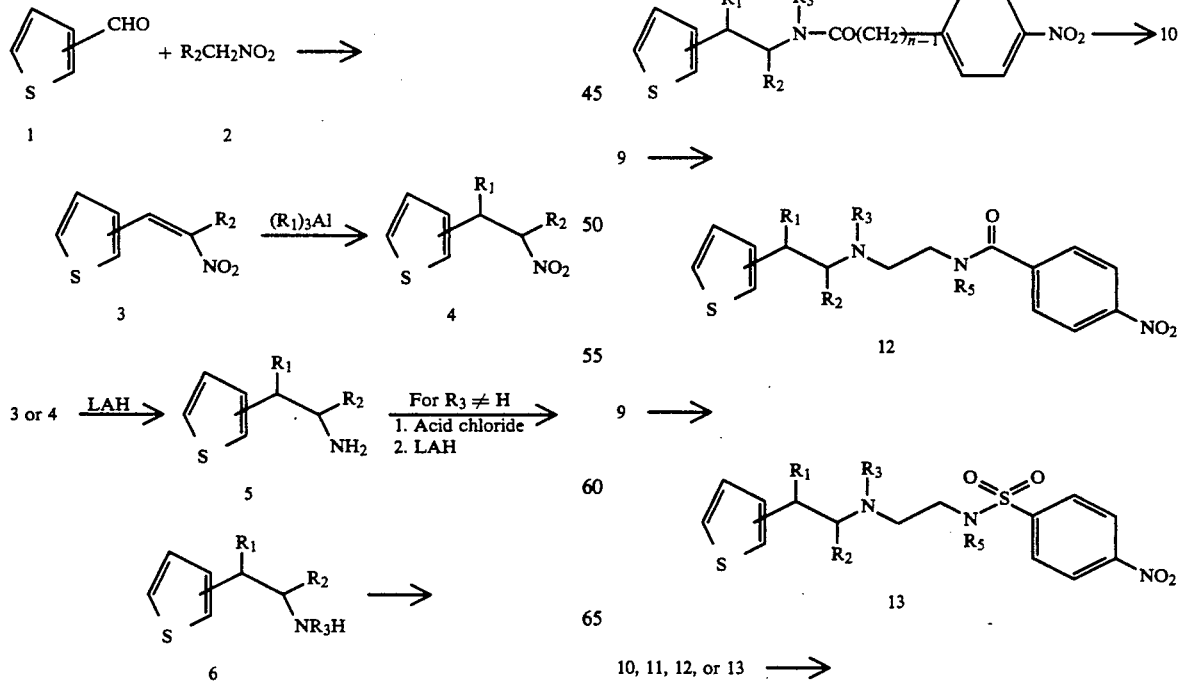

-continued

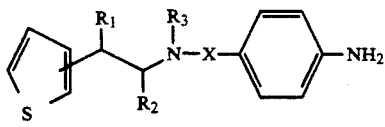

14

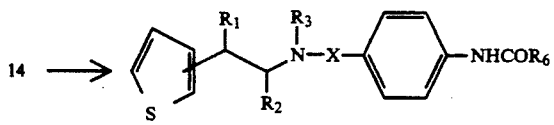

15

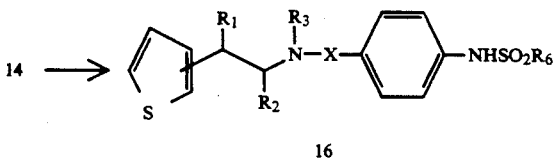

16

The synthesis begins with the Henry reaction between commercially available thiophene-2-carboxaldehyde or thiophene-3-carboxaldehyde 1 and a suitable nitroalkane 2 such as nitromethane, nitroethane or nitrobutane and with a suitable catalyst such as methylamine hydrochloride/sodium acetate/acetic acid or benzylamine/acetic acid present. This nitroalkene 3 is reacted with a commercially available trialkylaluminum such as trimethylaluminum, triethylaluminum or tripropylaluminum in an inert solvent such as methylene chloride, hexane or toluene. The nitro compounds 3 or 4 are then reduced with lithium aluminum hydride in an inert solvent such as ether, tetrahydrofuran, dimethoxyethane or dioxane. The aminoethylthiophenes 5 are reacted with a suitable acid chloride such as acetyl chloride, propionyl chloride, hexanoyl chloride or isobutyryl chloride in an inert solvent such as ether, methylene chloride, chloroform or toluene in the presence of a HCl scavenger such as triethylamine, pyridine or sodium bicarbonate. These intermediate amides are reduced with lithium aluminum hydride in an inert solvent such as ether, tetrahydrofuran, dimethoxyethane or dioxane.

The amines 6 are reacted with an excess of either chloroacetonitrile or bromoacetonitrile in an inert solvent such as acetonitrile, 2-propanol, acetone or tetrahydrofuran in the presence of a base such as triethylamine, pyridine, sodium bicarbonate or sodium carbonate to afford the nitriles 7. These nitriles are reduced with lithium aluminum hydride in an inert solvent such as ether, tetrahydrofuran, dimethoxyethane or dioxane to produce the primary amines 8. The secondary amines 9 are prepared by reductive amination methods using an alkyl carboxaldehyde and a reducing agent such as sodium cyanoborohydride in a solvent such as methanol. Alternatively the amine is converted first to a carboxamide and reduced with lithium aluminum hydride as described for the conversion of 5 to 6. The amines 6 are treated with a suitable 4-nitrophenyl alkyl p-toluenesulfonylalkyl (or methanesulfonylalkyl) or 4-nitrophenyl alkyl halide such as 4-nitrophenethyl p-toluenesulfonate, 4-(4-nitrophenyl)-1-butyl p-toluenesulfonate, 4-(4-nitrophenyl)-1-butyl methanesulfonate, 4-nitrophenethyl bromide or 4-(4-nitrophenyl)-1-butyl bromide in an inert solvent such as acetonitrile, acetone, 2-butanone or tetrahydrofuran in the presence of a catalyst such as sodium iodide or potassium iodide and a base such as triethylamine, pyridine, sodium bicarbonate or sodium carbonate to produce the nitrophenyl compounds 10. The amines 6 are also reacted with p-toluenesulfonylalkyl (or methanesulfonylalkyl) or haloalkyl 4-nitrophenylethers such as 2-(4-nitrophenoxy)ether p-toluenesulfonate, β-bromo-4-nitrophenetole or 3-chloropropyl-4-nitrophenyl ether in an inert solvent such as acetonitrile, acetone, 2-butanone or tetrahydrofuran in the presence of a catalyst such as sodium iodide or potassium iodide and a base such as triethylamine, pyridine, sodium bicarbonate or sodium carbonate to afford phenyl ether compounds 11.

An alternative synthesis of 10 can be accomplished by first reacting the amine 6 with a suitable carboxylic acid (as a melt) or with an acid chloride in an inert solvent such as methylene chloride, chloroform, ether or toluene and with a base such as triethylamine, pyridine or sodium bicarbonate present. The intermediate amide is then reduced with a suitable reagent such as diborane in an inert solvent such as ether, tetrahydrofuran (THF), dioxane or dimethoxyethane to afford the desired amine 10.

The amines 9 are treated with 4-nitrobenzoyl chloride in an inert solvent such as methylene chloride, chloroform, ether or toluene either with or without the presence of a catalytic amount of 4-dimethylaminopyridine and a HCl scavenger such as triethylamine, pyridine or sodium bicarbonate to produce the amides 12. Similar to the preparation of 12, 9 is treated with 4-nitrobenzenesulfonyl chloride to produce the sulfonamides 13. These phenyl nitro compounds 10, 11, 12 or 13 are then converted to the anilines 14 by any number of reducing methods such as iron in acetic acid, iron in dimethylformamide, ammonium formate with palladium black (or palladium on carbon), formic acid with palladium black (or palladium on carbon), nickel (II) chloride/sodium borohydride or palladium on carbon under a hydrogen atmosphere. These anilines are then converted to their corresponding amides 15 using a suitable acid chloride such as acetyl chloride, propionyl chloride, hexanoyl chloride, isobutyryl chloride or benzoyl chloride in an inert solvent such as methylene chloride, chloroform or toluene either in the presence or absence of a HCl scavenger such as triethylamine, pyridine or sodium bicarbonate.

In a fashion similar to that described for 15, the sulfonamides 16 are prepared using the necessary sulfonyl chlorides such as methanesulfonyl chloride or benzenesulfonyl chloride.

Compounds 6-9 represent novel intermediate compounds of the invention which are useful for preparing compounds 10-16, which are the novel 2- and 3-aminoethylthiophene compounds of the invention.

Reference will now be made in detail to preferred embodiments of the invention; examples of which are illustrated below. It should be noted that acid addition to compounds 10-16 produces pharmaceutically acceptable salts which are included in the scope of this invention.

Methods of preparation of such salts are described below or within the knowledge of those skilled in the art. Therapeutically active non-toxic addition salts of compounds 10-16 are prepared by treatment of the compounds of the invention with appropriate organic and inorganic acids such as hydrochloric, sulfuric, nitric, phosphoric acetic, glycolic, pyruvic, mandelic, oxalic and the like in a suitable solvent such as isopropyl alcohol.

The invention will now be illustrated by examples. The examples are not intended to be limiting of the present invention. In conjunction with the detailed and general description above, the examples provide further understanding of the present invention and outline a process for producing the compounds of the invention.

The following examples represent preferred embodiments of the compounds, compositions, processes and methods of the invention for satisfying the stated objects of the invention.

EXAMPLES

The following processes and procedures for preparing the compounds of the present invention correspond to those reaction schemes illustrated above. The procedures below describe with particularity the various chemical reactions and procedures utilized. Any methods, starting materials or reagents which are not particularly described are those which are known or would be generally known and available to those skilled in the art. Procedures from the following references, as described in the examples below were utilized to produce certain intermediate compounds utilized in the synthesis of the compounds of the invention: *J. Med. Chem.*, 1978, 21, 978; *J. Amer. Chem. Soc.*, 1954, 76,4466; *J. Org. Chem.*, 1950, 15, 807; and *Tetrahedron*, 1968, 24, 5721. The entire disclosure of these references are hereby incorporated herein by reference. The compounds of the invention (10–16) produced in accordance with the example schemes are identified below and designated by Example Numbers 1–31. The titled compounds may be produced as hydrochloride and dihdrochloride salts which is apparent from the description thereof and is not indicated in the title.

PREPARATION OF INTERMEDIATES 3–8

General Procedure for the Preparation of Nitroalkenes 3

The commercially available thiophene-2- or thiophene-3-carboxaldehyde (1 eq) was dissolved in a nitroalkane (4 eq) and treated with methylamine hydrochloride (0.4 eq), sodium acetate (0.4 eq) and glacial acetic acid (0.4 eq). This mixture was warmed to 55°–60° C. for 6 to 16 hours. After the volatiles had been removed under reduced pressure, the residue was treated with water. If a solid did not form, the aqueous mixture was extracted with methylene chloride and the combined extract s were dried ($Na_2SO_4$). Solvent removal produced the desired thiophene compound 3.

2-(2-Nitro-1-propenyl)thiophene

Prepared in quantitative yield. A sample was recrystallized from ether/hexane; mp 68°–70° C.

2-(2-Nitro-1-pentenyl)thiophene

Prepared in 93% yield. A sample was recrystallized from hexane to afford a bright yellow solid; mp 25°–25.5° C.; IR (KBr) 2963, 2933, 2873, 1637, 1514, 1501, 1463, 1436, 1421, 1377, 1332, 1304, 1278, 1242, 1215, 1054, 1009, 860 and 710 cm$^{-1}$. Elemental analysis calculated (Anal.Calc'd) for:

(Anal. Calc'd) for: $C_9H_{11}NO_2S$: C, 54.80; H, 5.62; N, 7.10. Found: C, 54.88; H, 5.58; N, 7.12.

3-(2-Nitro-1-propenyl)thiophene

Prepared in 94% yield. A sample was recrystallized from 2-propanol; mp 68°–69° C.

Anal. Calc'd for $C_7H_6NO_2S$: C, 49.68; H, 4.17; N, 8.28. Found: C, 49.69, H, 4.22; N, 8.05.

3-(2-Nitro-1-pentenyl)thiophene

Prepared as a yellow solid in 91% yield; mp 52°–54.5° C.; IR (KBr) 3113, 3103, 2962, 2948, 2928, 2871, 1642, 1517, 1504, 1434, 1338, 1307, 1276, 1250, 1168, 941, 866, 795 and 631 cm$^{-1}$.

Anal. Calc'd for $C_9H_{11}NO_2S$: C, 54.81; H, 5.62; N, 7.10. Found: C, 54.84; H, 5.60; N, 7.00.

3-(2-Nitroethenyl)thiophene

When $R_2$ is H the thiophene-3-carboxaldehyde (1 eq) was dissolved in 2-propanol and treated with nitromethane (1 eq), benzylamine (0.065 eq) and glacial acetic acid (0.13 eq). After 60 minutes of refluxing, the mixture was cooled, the solid was collected and washed with ice-cold ether to afford the product (56%); mp 94.5°–96.5° C.

General Procedure for the Preparation of Nitroalkenes 4

3-(1-Nitro-2-propyl)thiophene

When $R_2$ is H the 3-(2-nitroethenyl)thiophene (1 eq) was suspended in hexane, cooled in an ice bath under nitrogen and slowly treated with 2N trimethylaluminum in hexane (2.6 eq). After 30 minutes, the solution was quenched with 3N HCl, diluted with ether and filtered. The organic layer was dried ($Na_2SO_4$) and condensed under reduced pressure to afford the crude product. This material was purified by flash silica gel column chromatography using 70% hexane in methylene chloride. The product was obtained as a colorless oil (80%); MH+ at m/z 172.

General Procedure for the Preparation of Aminoalkenes 5

A THF or ether solution of the nitro compounds 3 or 4 (1 eq) was slowly added to an excess of LAH (2–4 eq) in either THF or ether under nitrogen (cooling maybe necessary). The reaction mixture was then either stirred at room temperature (rt) for 16 hours or warmed to reflux for 4–6 hours and then carefully quenched with a freshly prepared saturated $Na_2SO_4$ solution. The solid was removed and washed several times with solvent. The combined filtrate was condensed in vacuo to afford the crude product.

2-(2-Amino-1-propyl)thiophene

This material was prepared in 64% yield starting with 2-(2-nitro-1-propenyl)thiophene. A portion of this material was treated with HCl/2-propanol/ether to afford the hydrochloride salt; mp 143°–145.5° C.

2-(2-Amino-1-pentyl)thiophene

This material was prepared in 80% yield starting with 2-(2-nitro-1-pentenyl)thiophene; MH+ at m/z 170.

3-(2-Aminoethyl)thiophene

This material was prepared in 77% yield starting with 3-(2-nitroethenyl)thiophene. A portion of this material was treated with HCl/2-propanol to afford the hydrochloride salt; mp 208°–211.5° C.

Anal. Calc'd for $C_6H_9NS.HCl$: C, 44.03; H 6.16; N, 8.56; S, 19.59. Found: C, 44.03; H 6.21; N, 8.53; S, 19.39.

3-(2-Amino-1-propyl)thiophene

This material was prepared in 91% yield starting with 3-(2-nitro-1-propenyl)thiophene. A portion of this material was treated with HCl/2-propanol/ether to afford the hydrochloride salt; mp 135°–136.5° C.

3-(1-Amino-2-propyl)thiophene

This material was prepared in 98% yield starting with 3-(1-nitro-2-propyl)thiophene; an oil was obtained MH+ at m/z 142.

3-(2-Amino-1-pentyl)thiophene

This material was prepared in 96% yield starting with 3-(2-nitro-1-pentenyl)thiophene; MH+ at m/z 170. This material was treated with oxalic acid in acetone/ether to afford the oxalate salt; mp 90.5 (shrinks) 95°–99° C.; IR (KBr) 3184, 3089, 3015, 3006, 2960, 2933, 2875, 1741, 1733, 1719, 1702, 1652, 1635, 1617, 1590, 1560, 1540, 1500, 1467, 1404, 1279, 1219, 1122, 1112, 780 and 720 cm$^{-1}$.

Anal. Calc'd for $C_9H_{15}NS.C_2H_2O_4.1/4H_2O$: C, 50.09; H, 6.69; N, 5.31. Found: C, 50.39; H, 6.60; N, 5.30.

General Procedure for the Preparation of Aminoalkenes 6

A methylene chloride solution of the aminoethylthiophene 5 (1 eq), triethylamine (1.4 eq) and 4-dimethylaminopyridine (0.1 eq) at 0° C. under nitrogen was treated slowly with a methylene chloride solution of the necessary acid chloride (1.2 eq). The mixture was stirred at 0° C. (or rt) overnight and was quenched with aqueous citric acid. The methylene chloride layer was washed with brine and dried ($Na_2SO_4$) and then condensed in vacuo to afford the crude amide in quantitative yield. This material was either used directly in the next step or purified by flash silica gel chromatography.

The amide (1 eq) was then dissolved in ether and slowly added to an ethereal mixture of excess LAH (5 eq) under nitrogen (cooling may be necessary). The mixture was stirred at rt for 16–18 hours and then carefully quenched with a freshly prepared saturated $Na_2SO_4$ solution. The solid was removed and leached with hot ether. The combined filtrate was condensed in vacuo to afford the amine 6.

N-Ethyl 2-(2-amino-1-propyl)thiophene

This material was prepared as a light yellow oil in 90% yield starting with 2-(2-amino-1-propyl)thiophene from above; IR (neat) 3300, 3080, 1670, 1530, 1440, 1370, 1150 and 740 cm$^{-1}$.

N-Ethyl 2-(2-amino-1-pentyl)thiophene

This material was prepared as a yellow oil in 90% yield starting with 2-(2-amino-1-pentyl)thiophene from above; IR (neat) 3300, 3080, 1670, 1460, 1370, 1140 and 740 cm$^{-1}$.

3-(2-Aminoethyl)-N-ethylthiophene

This material was prepared as a yellow oil in 26% yield starting with 3-(2-aminoethyl)thiophene from above; IR (neat) 3300, 3100, 1660, 1530, 1370 and 770 cm$^{-1}$.

N-Ethyl 3-(2-amino-1-propyl)thiophene

This material was prepared as a yellow oil in 78% yield starting with 3-(2-amino-1-propyl)thiophene from above; IR (neat) 3300, 3080, 1660, 1450, 1370, 1130 and 740 cm$^{-1}$.

3-(2-Amino-1-propyl)-N-pentylthiophene

This material was prepared as a colorless oil in 100% yield starting with 3-(2-amino-1-propyl)thiophene from above; MH+ at m/z 212; IR (neat) 3300, 3080, 1660, 1450, 1370, 1130 and 740 cm$^{-1}$.

N-Ethyl 3-(2-Amino-1-pentyl)thiophene

This material was prepared as a colorless oil in 76% yield starting with 3-(2-amino-1-pentyl)thiophene from above; IR (neat) 3300, 3100, 1660, 1530, 1470, 1370, 1130 and 740 cm$^{-1}$.

N-Ethyl 3-(1-Amino-2-propyl)thiophene

This material was prepared as a yellow oil in 84% yield starting with 3-(1-amino-2-propyl)thiophene from above; MH+ at m/z 170; IR (neat) 3300, 3100, 2960, 2920, 2805, 1670, 1450, 1130, 850 and 775 cm$^{-1}$.

General Procedure for the Preparation of Cyanomethyl Amines 7

The aminoethyl compound 6 (1 eq) was reacted with an excess of chloroacetonitrile (8 eq) and $NaHCO_3$ (3 eq) in 2-propanol at reflux for 16 hours under nitrogen. After the solvent had been removed in vacuo, the residue was mixed as a slurry in methylene chloride and extracted with 6N HCl. The combined acidic extract was carefully treated with saturated $NaHCO_3$ until basic. This aqueous solution was extracted with methylene chloride and the combined extract was washed with brine and dried ($Na_2SO_4$). Solvent removal produced the desired product which was used directly in the next step or purified by flash silica gel column chromatography.

Ethyl-{2-[1-(thiophen-3-yl)propyl]amino}acetonitrile

The above compound was isolated in 50% yield as a yellow oil that was purified by flash silica gel column chromatography eluting with methylene chloride.

Ethyl-{1-[2-(thiophen-3-yl)propyl]amino}acetonitrile

The above compound was isolated in 60% yield as an oil; MH+ at m/z 209; IR (neat) 3010, 2980, 2820, 2240, 1540, 1460, 1430, 1390, 1340, 1100, 1080, 960, 870 and 780 cm$^{-1}$.

General Procedure for the Preparation of Ethanediamines 8

An ether solution of cyanomethyl compounds 7 (1 eq) was slowly added to an ethereal mixture of LAH (2 eq) under nitrogen (cooling maybe necessary). After stirring at rt for 2–16 hours the reaction mixture was carefully quenched with a freshly prepared saturated $Na_2SO_4$ solution. The solid was removed and leached with hot ether. The combined filtrate was condensed in vacuo to afford the aminoethyl amines 8.

N-Ethyl-N-[1-methyl-2-(thiophen-3-yl)ethyl]-1,2-ethanediamine

The above compound was isolated in quantitative yield as a yellow oil.

N-Ethyl-N-[2-methyl-2-(thiophen-3-yl)ethyl]-1,2-ethanediamine

The above compound was isolated in quantitative yield as a yellow oil.

Method A: General Procedure for the Preparation of Aminoethyl Compounds 10 or 11

To an acetonitrile solution of 2- or 3-thiophene aminoethyl compounds 6 (1 eq) was added either an alkyl methanesulfonate or alkyl halide (e.g. 4-(4-nitrophenyl)-1-butyl methanesulfonate [prepared by reacting 4-(4-nitrophenyl)butane-1-ol with methanesulfonyl chloride in methylene chloride and triethylamine and isolated as a crystalline solid from ether/hexane], 1-(2-chloroethoxy)-4-nitrobenzene or 1-(3-chloropropoxy)-4-nitrobenzene [prepared by reacting 4-nitrophenol (1 eq) with 1-bromo-3-chloropropane (1.5 eq) in methyl ethyl ketone with $K_2CO_3$ (2 eq) present and isolated as a yellow oil that was crystallized from ether/hexane, mp 37.5°–38.5° C.] (1.5–2.0 eq) and $K_2CO_3$ (5 eq) [for the chloro compounds, NaI (1.4–2 eq) was added]. The mixture was refluxed under nitrogen for 16–18 hours. After the solvent had been removed in vacuo, the oily solid was mixed as a slurry in water and extracted with methylene chloride. The combined methylene chloride extract was washed with water and brine and dried ($Na_2SO_4$). Solvent removal produced the crude product that was purified by flash silica gel chromatography using a mixture of ethyl acetate in hexane.

Method B: General Procedure for the Preparation of Compounds 12 or 13

To a methylene chloride suspension of either 4-nitrobenzoyl chloride or 4-nitrobenzenesulfonyl chloride (1.1 eq) was added a methylene chloride solution of the ethanediamine compounds 9. After stirring at rt for 16 hours the solid was removed by filtration. When triethylamine (3 eq) or pyridine was added, the free base of the product was isolated.

Method C: General Procedure for the Preparation of Aniline Compounds 14

To a methanol solution of nitro compounds 10, 11, 12 or 13 (1 eq) and nickel (II) chloride hexahydrate (2 eq) at 0° C. under nitrogen was added $NaBH_4$ (4 eq) in small portions. After stirring the mixture at rt for 16 hours it was concentrated to dryness and carefully treated with 10% HCl. The solids were removed and the filtrate was treated with concentrated $NH_4OH$ until basic and extracted with methylene chloride. The combined extracts were washed with water and brine and dried ($Na_2SO_4$). Solvent removal afforded the crude aniline as an oil that was purified by silica gel chromatography or directly converted to its hydrochloride salt.

Method D: General Procedure for the Preparation of 15 or 16

An ether solution of the aniline 14 (1 eq) was treated carefully with methanesulfonyl chloride (1.2 eq) [Alternatively, this reaction could be performed in methylene chloride and pyridine (5 eq)]. The mixture was stirred at rt for 0.33 to 16 hours and then treated with $NaHCO_3$ solution. The aqueous solution was extracted with methylene chloride and the combined extracts were washed with brine and dried ($Na_2SO_4$). Solvent removal produced the desired product.

EXAMPLE 1

N-Ethyl-N-[1-methyl-2-(2-thienyl)ethyl]-4-(4-nitrophenyl)butylamine

Prepared by Method A and isolated in 30% yield as a brown oil starting from N-ethyl 2-(2-amino-1-propyl)-thiophene; $MH^+$ at m/z 347; IR (neat) 3100, 3080, 3060, 2920, 1670, 1600, 1510, 1340, 1110, 850 and 745 $cm^{-1}$.

EXAMPLE 2

N-Ethyl-N-[1-propyl-2-(2-thienyl)ethyl]-4-(4-nitrophenyl)butylamine

Prepared by Method A and isolated in 10% yield as a brown oil starting from N-ethyl 2-(2-amino-1-pentyl)-thiophene; $MH^+$ at m/z 375; IR (neat) 3100, 3080, 3060, 2920, 1600, 1510, 1340, 1110 and 850 $cm^{-1}$.

EXAMPLE 3

N-Ethyl-4-(4-nitrophenyl)-N-[2-(3-thienyl)ethyl]butylamine

Prepared by Method A and isolated in 35% yield as a brown oil starting from N-ethyl 3-thiopheneethanamine; $MH^+$ at m/z 333; IR (neat) 3100, 3080, 3060, 2920, 1600, 1510, 1340, 1110, 850 and 740 $cm^{-1}$.

EXAMPLE 4

N-[1-Methyl-2-(3-thienyl)ethyl]-4-(4-nitrophenyl)-butylamine

A mixture of 3-(2-amino-1-propyl)thiophene (5.65 g, 40 mmol) and 4-(4-nitrophenyl)butyric acid (8.37 g, 40 mmol) was heated to 120° C. under nitrogen for 16 hours. The solid was dissolved in methylene chloride and washed with 1N HCl, 5% $Na_2CO_3$ and brine and dried ($MgSO_4$). Solvent removal produced the crude amide which was purified by flash silica gel column chromatography using ether as the eluent (6.07 g, 46%).

This amide (6.07 g, 18.3 mmol) was dissolved in THF and carefully treated with $BH_3$/THF (55 ml, 55 mmol) under nitrogen. The mixture was refluxed for 18 hours treated with another portion of $BH_3$/THF (55 ml, 55 mmol) and then refluxed for an additional 5 days. The solution was quenched carefully with water. After the solvent had been removed in vacuo, the residue was dissolved in methanol and HCl gas was bubbled through the solution at rt. This solution was stored at rt for 18 hours and then treated with 2N NaOH until basic. The aqueous solution was extracted with methylene chloride and the combined extracts were washed with water and brine and dried ($MgSO_4$). Solvent removal produced the crude product which was purified by flash silica gel column chromatography using 4% methanol in methylene chloride. The product was obtained as a golden-brown oil which was dissolved in 2-propanol and treated with HCl/IPA (1.1 eq). The hydrochloride salt was isolated as a beige solid; mp 183°–185° C.; IR (KBr) 2950, 2790, 2750, 2550, 2470, 1605, 1510, 1305, 865, 790 and 710 $cm^{-1}$.

Anal. Calc'd for $C_{17}H_{22}N_2O_2S\cdot HCl$: C, 57.53; H, 6.53; N, 7.89. Found: C, 57.41; H, 6.34; N, 7.61.

EXAMPLE 5

N-Ethyl-N-[1-methyl-2-(3-thienyl)ethyl]-4-(4-nitrophenyl)butylamine

Prepared by Method A and isolated in 45% yield as a yellow oil starting from N-ethyl 3-(2-amino-1-propyl)-thiophene. The hydrochloride salt was prepared as above to afford an off-white solid; mp 89°-93° C.; MH+ at m/z 347; IR of free base (neat) 3100, 3080, 3060, 2920, 1600, 1510, 1350, 1110 and 850 cm$^{-1}$.

Anal. Calc'd for $C_{19}H_{26}N_2O_2S.HCl.H_2O$: C, 56.92; H, 7.28; N, 6.98. Found: C, 57.06; H, 7.24; N, 6.88.

EXAMPLE 6

N-Ethyl-N-[1-propyl-2-(3-thienyl)ethyl]-4-(4-nitrophenyl)butylamine

Prepared by Method A and isolated in 3.5% yield as a yellow oil starting from N-ethyl 3-(2-amino-1-pentyl)-thiophene; MH+ at m/z 375; IR (neat) 3100, 3080, 3060, 2920, 1600, 1510, 1340, 1110, 850 and 740 cm$^{-1}$.

EXAMPLE 7

N-[1-Methyl-2-(3-thienyl)ethyl]-N-pentyl-4-(4-nitrophenyl)butylamine

Prepared by Method A (NaI added; 1.4 eq) and isolated in 35% yield as a yellow oil starting from 3-(2-amino-1-propyl)-N-pentylthiophene; MH+ at m/z 389; IR (neat) 3100, 3080, 3060, 2910, 1600, 1520, 1340, 1110 and 850 cm$^{-1}$.

EXAMPLE 8

N-Ethyl-N-[1-methyl-2-(3-thienyl)ethyl]-2-(4-nitrophenoxy)ethylamine

Prepared by Method A and isolated in 30% yield as a yellow oil starting from N-ethyl 3-(2-amino-1-propyl)-thiophene. The hydrochloride salt was prepared as above to afford an off-white solid; mp 117°-121° C.; MH+ at m/z 335; IR of free base (neat) 3110, 3080, 3060, 1605, 1590, 1510, 1500, 1340, 1260, 1170, 1110, 840, 770 and 750 cm$^{-1}$.

Anal. Calc'd for $C_{17}H_{22}N_2O_3S.HCl$: C, 55.05; H, 6.28; N, 7.55. Found: C, 54.96; H, 6.32; N, 7.55.

EXAMPLE 9

N-Ethyl-N-[1-methyl-2-(3-thienyl)ethyl]-2-(4-nitrophenoxy)propylamine

Prepared by Method A and isolated in 65% yield as an oil starting from N-ethyl 3-(2-amino-1-propyl)thiophene; MH+ at m/z 349; IR (neat) 3100, 3080, 2920, 1600, 1590, 1510, 1380, 1260, 1170, 1100, 840 and 750 cm$^{-1}$.

EXAMPLE 10

N-Ethyl-N-[1-methyl-2-(3-thienyl)ethyl]-2-(4-nitrobenzamido)ethylamine

Prepared by Method B and isolated in 94% yield as a white solid starting with N-ethyl-N-[1-methyl-2-(thiophen-3-yl)ethyl]-1,2-ethanediamine; mp 200°-203° C.; MH+ at m/z 362; IR (KBr) 3360, 3100, 3080, 2910, 1730, 1660, 1650, 1600, 1530, 1340, 910, 870, 780 and 730 cm$^{-1}$.

Anal. Calc'd for $C_{18}H_{23}N_3O_3S.HCl$: C, 54.33; H, 6.08; N, 10.56. Found: C, 53.92; H, 6.08; N, 10.38.

EXAMPLE 11

N-Ethyl-N-[1-methyl-2-(3-thienyl)ethyl]-2-(4-nitrobenzenesulfonamido)ethylamine

Prepared by Method B [triethylamine(TEA) as base and 4-dimethylaminopyridine (0.5 eq) as a catalyst] and isolated as an oil which was converted to its hydrochloride salt (light gray solid, 50% yield starting with N-ethyl-N-[1-methyl-2-(thiophen-3-yl)ethyl]-1,2-ethanediamine); mp 156°-159° C.; MH+ at m/z 398; IR (KBr) 3300, 3100, 2920, 1600, 1530, 1350, 1090 and 850 cm$^{-1}$.

Anal. Calc'd for $C_{17}H_{23}N_3O_3S_2.HCl$: C, 47.05; H, 5.60; N, 9.68. Found: C, 47.13; H, 5.59; N,-9.60.

EXAMPLE 12

N-Ethyl-N-[2-methyl-2-(3-thienyl)ethyl]-2-(4-nitrobenzamido)ethylamine

Prepared by Method B (pyridine as base) and isolated as its hydrochloride salt (off-white solid, 47% yield starting with N-ethyl-N-[2-methyl-2-(thiophen-3-yl)ethyl]-1,2-ethanediamine); mp 125°-130° C.; IR (KBr) 3300, 3215, 2927, 1666, 1604, 1530, 1348, 1090 and 850 cm$^{-1}$.

Anal. Calc'd for $C_{18}H_{23}N_3O_3S.HCl$: C, 54.33; H, 6.08; N, 10.56. Found: C, 54.00; H, 6.02; N, 10.31.

EXAMPLE 13

4-(4-Aminophenyl)-N-ethyl-N-[1-methyl-2-(2-thienyl)ethyl]butylamine

Prepared by Method C starting with the compound in Example 1 and isolated in quantitative yield as a colorless oil; MH+ at m/z 317; IR (neat) 3460, 3360, 3320, 1620, 1520, 1370, 1130 and 830 cm$^{-1}$.

EXAMPLE 14

4-(4-Aminophenyl)-N-ethyl-N-[1-propyl-2-(2-thienyl)ethyl]butylamine

Prepared by Method C starting with the compound in Example 2 and isolated in quantitative yield as a yellow oil; MH+ at m/z 345; IR (neat) 3420, 3340, 3100, 1620, 1510, 1450, 1370, 810, 730 and 680 cm$^{-1}$.

EXAMPLE 15

4-(4-Aminophenyl)-N-ethyl-N-[2-(3-thienyl)ethyl]-butylamine

Prepared by Method C starting with the compound in Example 3 and isolated in 67% yield as a yellow oil. The dihydrochloride salt was prepared from HCl/IPA to afford a white crystalline solid; mp 182°-184° C.; MH+ at m/z 345; IR of the free base (neat) 3440, 3360, 3200, 3100, 1620, 1510, 1270, 1130 and 820 cm$^{-1}$.

Anal. Calc'd for $C_{18}H_{26}N_2S.2HCl$: C, 57.59; H, 7.51; N, 7.45. Found: C, 57.83; H, 7.81; N, 7.39.

EXAMPLE 16

4-(4-Aminophenyl)-N-ethyl-N-[1-methyl-2-(3-thienyl)ethyl]butylamine

A suspension of the compound in Example 5 (2.4 g, 6.9 mmol) with iron fillings (1.8 g, 32.2 g atom) in ethanol at 0° C. was slowly treated dropwise with 6 N HCl (72 ml). After the mixture had been stirred at rt for 16 hours it was filtered and the filtrate was treated with 50% NaOH until basic. This mixture was filtered, the ethanol was removed in vacuo and the aqueous filtrate was extracted with methylene chloride. The combined extract was washed with water and brine and dried ($Na_2SO_4$). Solvent removal produced the crude product that was purified by silica gel column chromatography using acetone as eluent to afford the desired product in 90% yield as a yellow oil. The dihydrochloride salt was prepared from HCl/IPA to afford an off-white solid; mp 208°-211° C.; MH+ at m/z 317; IR of the free base (neat) 3480, 3360, 3100, 1640, 1540 and 840 cm$^{-1}$.

Anal. Calc'd for $C_{19}H_{28}N_2S·2HCl$: C, 58.62; H, 7.78; N, 7.19. Found: C, 58.77; H, 7.55; N, 6.99.

EXAMPLE 17

4-(4-Aminophenyl)-N-ethyl-N-[1-propyl-2-(3-thienyl)ethyl]butylamine

Prepared by Method C starting with the compound in Example 6 and isolated in 90% yield as a yellow oil; MH+ at m/z 345; IR (neat) 3460, 3380, 3220, 3100, 1630, 1520, 1370, 1270, 1130 and 830 cm$^{-1}$.

EXAMPLE 18

4-(4-Aminophenyl)-N-pentyl-N-[1-methyl-2-(3-thienyl)ethyl]butylamine

Prepared by Method C starting with the compound in Example 7 and isolated in 85% yield as a colorless oil. The dihydrochloride salt was prepared from HCl/IPA to afford a light brown foam; mp 165°–170° C.; IR of the free base (neat) 3460, 3380, 3200, 1620, 1510, 1370, 1270, 1130 and 830 cm$^{-1}$.

Anal. Calc'd for $C_{22}H_{34}N_2S·2HCl·1/4H_2O$: C, 60.63; H, 8.44; N, 6.42. Found: C, 60.44; H, 8.45; N, 6.38.

EXAMPLE 19

2-(4-Aminophenoxy)-N-ethyl-N-[1-methyl-2-(3-thienyl)ethyl]ethylamine

Prepared by Method C starting with the compound in Example 8 and isolated in 80% yield as a colorless oil; MH+ at m/z 305; IR (neat) 3420, 3360, 3200, 3100, 1620, 1510, 1370, 1240, 1030 and 830 cm$^{-1}$.

EXAMPLE 20

3-(4-Aminophenoxy)-N-ethyl-N-[1-methyl-2-(3-thienyl)ethyl]propylamine

Prepared by Method C starting with the compound in Example 9 and isolated after column chromatography [EtOAc in hexane (1:1)] in 60% yield as an oil; MH+ at m/z 319; IR (neat) 3440, 3360, 3220, 3100, 2920, 1630, 1610, 1510, 1240 and 830 cm$^{-1}$.

EXAMPLE 21

2-(4-Aminobenzamido)-N-ethyl-N-[1-methyl-2-(3-thienyl)ethyl]ethylamine

Prepared by Method C starting with the compound in Example 10 and isolated in 80% yield as a light purple oil; IR (neat) 3460, 3340, 3220, 1640, 1630, 1600, 1500, 1380, 1180 and 840 cm$^{-1}$.

EXAMPLE 22

2-(4-Aminobenzenesulfonamido)-N-ethyl-N-[1-methyl-2-(3-thienyl)ethyl]ethylamine

Prepared by Method C starting with the compound in Example 11 and isolated in 60% yield as a colorless oil. The hydrochloride salt was prepared from HCl/IPA to afford a white crystalline solid; mp 122°–126° C.; MH+ at m/z 368; IR of the free base (neat) 3470, 3360, 3240, 3100, 1630, 1590, 1500, 1390, 1150, 1090 and 830 cm$^{-1}$.

EXAMPLE 23

2-(4-Aminobenzamido)-N-ethyl-N-[2-methyl-2-(3-thienyl)ethyl]ethylamine

Prepared by Method C starting with the compound in Example 12 and isolated in 85% yield as a yellow oil. The dihydrochloride salt was prepared from HCl/IPA to afford a yellow foam; mp 203°–206° C.; MH+ at m/z 332; IR of the free base (neat) 3490, 3360, 3240, 3010, 2980, 2820, 1650, 1640, 1610, 1580, 1540, 1510, 1280, 1180, 1070, 850, 790, and 750 cm$^{-1}$.

Anal. Calc'd for $C_{18}H_{25}N_3S·2HCl$: C, 53.46; H, 6.72; N, 10.35. Found: C, 53.52; H, 7.01; N, 10.11.

EXAMPLE 24

N-Ethyl-4-(4-methanesulfonylaminophenyl)-N-[2-[3-(2-thienyl)]propyl]butylamine

Prepared by Method D starting with the compound in Example 13 and isolated in 80% yield as a gum. The hydrochloride salt was prepared from HCl/IPA to afford a yellow crystalline solid; mp 75°–80° C.; MH+ at m/z 395; IR (KBr) 3420, 3080, 2940, 2660, 2490, 1610, 1510, 1330, 1150, 970, 830, and 770 cm$^{-1}$.

Anal. Calc'd for $C_{20}H_{30}N_2O_2S_2·HCl$: C, 55.74; H, 7.24; N, 6.50. Found: C, 55.42; H, 7.30; N, 6.70.

EXAMPLE 25

N-Ethyl-4-(4-methanesulfonylaminophenyl)-N-[1-propyl-2-(2-thienyl)ethyl]butylamine Prepared by Method D using methylene chloride/pyridine and starting with the compound in Example 14. Solvent removal produced an orange oil which was treated with HCl/IPA to afford the hydrochloride salt as a brown glassy powder (23%); mp 49°–55° C.; MH+ at m/z 423; IR of the free base (neat) 3260, 3010, 2920, 1610, 1510, 1450, 1360, 1150, 850 and 740 cm$^{-1}$.

Anal. Calc'd for $C_{22}H_{34}N_2O_2S_2·HCl$: C, 57.59; H, 7.67; N, 6.10. Found: C, 57.14; H, 7.84; N, 5.92.

EXAMPLE 26

N-Ethyl-4-(4-methanesulfonylaminophenyl)-N-[1-methyl-2-(3-thienyl)ethyl]butylamine Prepared by Method D starting with the compound in Example 16 and isolated directly as the hydrochloride salt (brown glassy solid) in 95% yield; mp 60°–63° C.; MH+ at m/z 395; IR of the free base (neat) 3260, 3110, 3020, 2920, 1610, 1590, 1510, 1450, 1320, 1150, 970 and 910 cm$^{-1}$.

Anal. Calc'd for $C_{20}H_{30}N_2O_2S_2·HCl$: C, 55.74; H, 7.24; N, 6.50. Found: C, 55.54; H, 7.60; N, 6.27.

EXAMPLE 27

N-Ethyl-4-(4-methanesulfonylaminophenyl)-N-[1-propyl-2-(3-thienyl)ethyl]butylamine Prepared by Method D using ether/pyridine as solvent and starting with the compound in Example 17. The hydrochloride salt was isolated directly from the reaction as a yellow crystalline solid (75% yield); mp 80°–83° C.; IR (KBr) 2940, 1512, 1332, 1222, 1153 and 772 cm$^{-1}$.

Anal. Calc'd for $C_{22}H_{34}N_2O_2S_2·HCl·3/2H_2O$: C, 54.38; H, 7.88; N, 5.76. Found: C, 54.35; H, 7.60; N, 6.10.

EXAMPLE 28

N-Ethyl-2-(4-methanesulfonylaminophenoxy)-N-[1-methyl-2-(3-thienyl)ethyl]ethylamine Prepared by Method D starting with the compound in Example 19 and isolated in quantitative yield as a yellow oil. This material was treated with HCl/IPA to afford the hydrochloride salt as an off-white solid; mp 156°–159° C.; MH+ at m/z 383; IR of the free base (neat) 3260, 3100, 2920, 1610, 1510, 1460, 1390, 1320, 1240, 1150 and 830 cm$^{-1}$.

Anal. Calc'd for $C_{18}H_{26}N_2O_3S_2 \cdot HCl$: C, 51.60; H, 6.51; N, 6.68. Found: C, 51.53; H, 6.57; N, 6.60.

EXAMPLE 29

N-Ethyl-3-(4-methanesulfonylaminophenoxy)-N-[1-methyl-2-(3-thienyl)ethyl]propylamine Prepared by Method D using methylene chloride/pyridine and starting with the compound in Example 20. The crude material was converted to its HCl salt with HCl/IPA to afford a light brown foam (10% yield); mp 68°–73° C.; IR (KBr) 2950, 1510, 1328, 1247, 1216, 1153, 970, 833 and 770 cm$^{-1}$.

Anal. Calc'd for $C_{19}H_{28}N_2O_3S_2 \cdot HCl$: C, 52.71; H, 6.76; N, 6.47. Found: C, 52.63; H, 7.14; N, 6.17.

EXAMPLE 30

N-Ethyl-2-(4-methanesulfonylaminobenzamido)-N-[1-methyl-2-(3-thienyl)ethyl]ethylamine Prepared by Method D using methylene chloride/pyridine and starting with the compound in Example 21. The product was obtained in 57% yield as a yellow oil. This material was treated with HCl/IPA to afford a pink crystalline solid; mp 127°–132° C.; MH+ at m/z 410; IR of the free base (neat) 3380, 3260, 3100, 3040, 2920, 1630, 1570, 1540, 1500, 1330, 1150, 970, 850 and 760 cm$^{-1}$.

Anal. Calc'd for $C_{19}H_{27}N_3O_3S_2 \cdot HCl$: C, 51.18; H, 6.32; N 9.42. Found: C, 51.40; H, 6.62; N, 9.24.

EXAMPLE 31

N-Ethyl-2-(4-methanesulfonylamidobenzenesulfonamido)-N-[1-methyl-2-(3-thienyl)ethyl]ethylamine Prepared by Method D using methylene chloride/pyridine and starting with the compound in Example 22. The product was obtained in 34% yield as an oil. This material was treated with HCl/IPA to afford a white powdery solid; mp 130°–136° C.; MH+ at m/z 446; IR of the free base (neat) 3360, 3100, 2920, 1600, 1500, 1460, 1330, 1150, 960, 840 and 780 cm$^{-1}$.

Anal. Calc'd for $C_{18}H_{27}N_3O_4S_3 \cdot HCl$: C, 44.86; H, 5.85; N, 8.72. Found: C, 45.24; H, 6.30; N, 8.31.

EXAMPLE 32

Biological Materials and Methods

A. General Procedure

Papillary muscles were dissected from the right ventricle of anesthetized male ferrets. The tendons of papillary muscles from the right ventricle were tied securely with a fine silk suture and then cut proximal to the tie. The distal connection of the muscle in the ventricular wall was cut and secured to a holder/stimulator. The tied tendon was attached to a force transducer (Grass FT-03) and the muscle was stretched to approximately 0.4 grams of tension. Papillary muscles were then placed in tissue baths containing 55 ml of Tyrode's solution of the following composition (mM): NaCl, 130.0; KCl, 4.0; MgCl$_2$, 1.0; NaHCO$_3$, 25.0; KH$_2$PO$_4$, 1.2; CaCl$_2$, 2.0; Dextrose, 11.0, pH 7.3, gassed with 5% CO$_2$–95% O$_2$. Temperature was normally 37° C. Isometric force was recorded during stimulation with constant current pulses (3 msec; 1.3×threshold) at frequencies between 0.2 and 3.3 Hz using platinum bipolar electrodes. Normally, 0.1 μM timolol was present continuously to prevent variations in tension produced by spontaneous or stimulation-induced release of catecholamines.

B. Measurement of Effective Refractory Period (ERP)

The ERP was determined using the extra-stimulus technique. Papillary muscles were paced using a trains of 20 or 10 basic stimuli (S1) at cycle lengths (S1-S1 interval) of 300 msec (3.33 Hz) and 1000 msec (1 Hz), respectively. Following each 20$^{th}$ or 10$^{th}$ basic contraction an extra-stimulus (S2) of equal intensity and duration was introduced at gradually decreasing coupling intervals (S1-S2 interval) until activation of the muscle failed to occur. The ERP was defined as the shortest S1-S2 interval in msec that produced activation of the muscle. Measurements were made to the nearest 2 msec decrement. The mean dose that produced a 20% increase in ERP is defined as ERP$_{20}$ and is reported in Example 33 (Table 1) in μM ($1 \times 10^{-6}$) units.

C. Measurement of Transmembrane Potential and Tension

Papillary muscles were pinned at the base to the SYLGARD® bottom of a 1.0 ml tissue bath. A silk suture was tied to the tendon and attached to a tension transducer (Grass FT-03) for measuring isometric force. Muscles were superfused at a rate of 5 ml/minutes with Tyrode's solution of the following composition (mM): NaCl, 130.0; KCl, 4.0; MgCl$_2$, 1.0; NaHCO$_3$, 24.0; NaH$_2$PO$_4$, 1.0; CaCl$_2$, 1.8; Dextrose, 5.6, pH 7.3. gassed with 5% CO$_2$–95% O$_2$. Temperature was normally 35° C. Muscles were stimulated with constant current pulses (0.1–0.3 msec; 2×threshold) at frequencies between 0.2 and 3.3 Hz using platinum bipolar electrodes. Transmembrane action potentials were measured using standard microelectrode techniques. Glass micro-capillary pipettes filled with 3M KCl($\approx$50 Mohms) were coupled to a high input-impedance, capacitance-neutralizing amplifier (e.g. WPI 773). Action potentials and isometric tension were displayed simultaneously on an oscilloscope (e.g. TEKTRONIX 11402, digital) and were analyzed using a computerized data acquisition system.

D. Compound Preparation

Test compounds were dissolved initially in dimethylsulfoxide (DMSO) at a stock concentration of $1 \times 10^{-2}$M and further dilutions were made directly in Tyrode's solution to achieve the final concentrations. Timolol was dissolved in water at a stock concentration of $1 \times 10^{-3}$M and was added directly to the Tyrode's solution bath to achieve a final concentration of $1 \times 10^{-7}$M. Test compounds were applied by serially increasing concentrations and measurements were taken at 15 minutes after addition of each concentration. The mean dose that produced a 20% increase in ERP is defined as ERP$_{20}$ and is reported in Example 33 (Table 1) in μM ($1 \times 10^{-6}$) units.

EXAMPLE 33

TABLE 1

Summary Table of Preparation Methods and Biological Activity

| Example # | Proc. Method | ERP$_{20}$ (μM) |
|---|---|---|
| 4 | amide/LAH | 0.7 |
| 5 | A | 0.045 |
| 8 | A | 0.21 |
| 10 | B | 0.08 |
| 11 | B | 1.2 |
| 12 | B | 1.0 |
| 15 | C | 1.2 |
| 16 | Fe/HCl | 1.5 |
| 18 | C | 1.5 |
| 22 | C | 1.5 |
| 23 | C | 10.0 |

TABLE 1-continued
Summary Table of Preparation Methods and Biological Activity

| Example # | Proc. Method | ERP$_{20}$ ($\mu$M) |
|---|---|---|
| 24 | D | 0.25 |
| 25 | D (CH$_2$Cl$_2$/Py) | 1.4 |
| 26 | D | 0.3 |
| 27 | D (CH$_2$Cl$_2$/Py) | 0.4 |
| 28 | D | 0.13 |
| 29 | D (CH$_2$Cl$_2$/Py) | 0.12 |
| 30 | D (CH$_2$Cl$_2$/Py) | 0.03 |
| 31 | D (CH$_2$Cl$_2$/Py) | 0.24 |

The above test results demonstrate the utility of the compounds of the invention for increasing the effective refractory periods in a mammal, i.e. male ferrets. The prolongation of effective refractory periods is believed to be an effective means of preventing or terminating atrial and ventricular arrhythmias which in turn may inhibit sudden cardiac death.

Pharmaceutical compositions containing compounds of the invention may comprise the compound of the present invention and a pharmaceutically acceptable carrier in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methyl cellulose, sodium carbosyl methyl cellulose, and the like. Liquid form preparations include solutions which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Aqueous solutions for oral administration can be prepared by dissolving the active compound in water and adding suitable flavorants, coloring agents, stabilizers and thickening agents as required. Aqueous suspensions for oral use can be made by dispersing the finely divided active component in water together with a viscous material such as a natural or synthetic gum, methyl cellulose, sodium carboxy methyl cellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as is disclosed for example by *Remington's Pharmaceutical Sciences*, Mack Publishing Co., Part 8 Chapters 76–93, "Pharmaceutical Preparations and Their Manufacture", pp. 1409–1677 (1985).

In thereapeutic use as antiarrythmic agents, the compounds utilized in the methods of this invention may be administered to a patient either orally or parenterally at efective dosage levels of from about 50–500 mg per day and preferably about 50 mg per day. The dosages, however, may be varied depending upon the results of specific clinical testing, the requirements of the patient, the weight and age of the patient, the severity of the condition being treated, and the compound being employed. Determination of optimum dosages for a particular situation is within the skill of the art.

The scope of the present invention is not limited by the description, examples and suggested uses herein; modifications can be made without departing from the spirit of the invention. For example, additional medicaments or active components may be used in combination with the compounds of the invention. Further, the novel compounds of the invention may be used in combination themselves as antiarrythmic agents or have other uses in addition to those described herein.

Applications of the compounds, compositions and methods of the present invention for medical or pharmaceutical uses can be accomplished by any clinical, medical, and pharmaceutical methods and techniques as are presently or prospectively known to those skilled in the art. Thus it is intended that the invention cover any modifications and variations of this invention provided that they come within the scope of the appended claims and their equivalents.

What is claimed is:

1. A compound of the following formula:

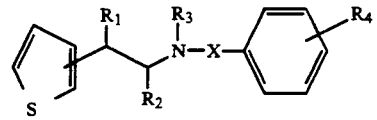

where

R$_1$ and R$_2$ are the same or different and are hydrogen, C$_1$–C$_4$ alkyl, C$_3$–C$_5$ branched chain alkyl, aryl, phenyl or substituted aryl or phenyl where the substituents are halogen, C$_1$–C$_6$ alkyl or C$_1$–C$_6$ alkoxy;

R$_3$ is hydrogen, C$_1$–C$_6$ alkyl or C$_3$–C$_5$ branched chain alkyl;

X is (CH$_2$)$_n$, (CH$_2$)$_{n+1}$O, (CH$_2$)$_2$NR$_5$CO, or (CH$_2$)$_2$NR$_5$SO$_2$;

R$_4$ is a mono-, di- or tri-sustituent which may be the same or different and is halogen, NO$_2$, NH$_2$, NHCOR$_6$ or NHSO$_2$R$_6$;

n is 1–5;

R$_5$ is hydrogen, C$_1$–C$_4$ alkyl or C$_3$–C$_5$ branched chain alkyl;

R$_6$ is C$_1$–C$_4$ alkyl, C$_3$–C$_5$ branched chain alkyl or phenyl; and substantially pure stereoisomers and pharmaceutically acceptable salts thereof.

2. The compound according to claim 1 wherein R$_1$ and R$_2$ are hydrogen or C$_1$–C$_3$ alkyl; R$_3$ is hydrogen or C$_1$–C$_5$ alkyl; R$_4$ is NO$_2$ or NHSO$_2$R$_6$; n is 2–4; R$_5$ is hydrogen; and R$_6$ is methyl.

3. The compound according to claim 1 selected from the group consisting of:

N-Ethyl-N-[1-methyl-2-(2-thienyl)ethyl]-4-(4-nitrophenyl)butylamine;
N-Ethyl-N-[1-propyl-2-(2-thienyl)ethyl]-4-(4-nitrophenyl)butylamine;
N-Ethyl-4-(4-nitrophenyl)-N-[2-(3-thienyl)ethyl]butylamine;
N-[1-Methyl-2-(3-thienyl)ethyl]-4-(4-nitrophenyl)butylamine;
N-Ethyl-N-[1-methyl-2-(3-thienyl)ethyl]-4-(4-nitrophenyl)butylamine;
N-Ethyl-N-[1-propyl-2-(3-thienyl)ethyl]-4-(4-nitrophenyl)butylamine;
N-[1-Methyl-2-(3-thienyl)ethyl]-N-pentyl-4-(4-nitrophenyl)butylamine;
N-Ethyl-N-[1-methyl-2-(3-thienyl)ethyl]-2-(4-nitrophenoxy)ethylamine;
N-Ethyl-N-[1-methyl-2-(3-thienyl)ethyl]-2-(4nitrophenoxy)propylamine;
N-Ethyl-N-[1-methyl-2-(3-thienyl)ethyl]-2-(4-nitrobenzamido)ethylamine;
N-Ethyl-N-[1-methyl-2-(3-thienyl)ethyl]-2-(4-nitrobenzenesulfonamido)ethylamine;
N-Ethyl-N-[2-methyl-2-(3-thienyl)ethyl]-2-(4-nitrobenzamido)ethylamine;
4-(4-Aminophenyl)-N-ethyl-N-[1-methyl-2-(2-thienyl)ethyl]butylamine;
4-(4-Aminophenyl)-N-ethyl-N-[1-propyl-2-(2-thienyl)ethyl]butylamine;
4-(4-Aminophenyl)-N-ethyl-N-[2-(3-thienyl)ethyl]butylamine;
4-(4-Aminophenyl)-N-ethyl-N-[1-methyl-2-(3-thienyl)ethyl]butylamine;
4-(4-Aminophenyl)-N-ethyl-N-[1-propyl-2-(3-thienyl)ethyl]butylamine;
4-(4-Aminophenyl)-N-pentyl-N-[1-methyl-2-(3-thienyl)ethyl]butylamine;
2-(4-Aminophenoxy)-N-ethyl-N-[1-methyl-2-(3-thienyl)ethyl]ethylamine;
3-(4-Aminophenoxy)-N-ethyl-N-[1-methyl-2-(3-thienyl)ethyl]propylamine;
2-(4-Aminobenzamido)-N-ethyl-N-[1-methyl-2-(3-thienyl)ethyl]ethylamine;
2-(4-Aminobenzenesulfonamido)-N-ethyl-N-[1-methyl-2-(3-thienyl)ethyl]ethylamine;
2-(4-Aminobenzamido)-N-ethyl-N-[2-methyl-2-(3-thienyl)ethyl]ethylamine;
N-Ethyl-4-(4-methanesulfonylaminophenyl)-N-[2-[3-(2-thienyl)]propyl]butylamine;
N-Ethyl-4-(4-methanesulfonylaminophenyl)-N-[1-propyl-2-(2-thienyl)ethyl]butylamine;
N-Ethyl-4-(4-methanesulfonylaminophenyl)-N-[1-methyl-2-(3-thienyl)ethyl]butylamine
N-Ethyl-4-(4-methanesulfonylaminophenyl)-N-[1-propyl-2-(3-thienyl)ethyl]butylamine
N-Ethyl-2-(4-methanesulfonylaminophenoxy)-N-[1-methyl-2-(3-thienyl)ethyl]ethylamine;
N-Ethyl-3-(4-methanesulfonaminophenoxy)-N-[1-methyl-2-(3-thienyl)ethyl]propylamine;
N-Ethyl-2-(4-methanesulfonylaminobenzamido)-N-[1-methyl-2-(3-thienyl)ethyl]ethylamine; and
N-Ethyl-2-(4-methanesulfonylamidobenzenesulfonamido)-N-[1-methyl-2-(3-thienyl)ethyl]ethylamine.

4. The compound according to claim 1 selected from the group consisting of:
N-[1-Methyl-2-(3-thienyl)ethyl]-4-(4-nitrophenyl)butylamine;
N-Ethyl-N-[1-methyl-2-(3-thienyl)ethyl]-4-(4-nitrophenyl)butylamine;
N-Ethyl-N-[1-methyl-2-(3-thienyl)ethyl]-2-(4-nitrophenoxy)ethylamine;
N-Ethyl-N-[1-methyl-2-(3-thienyl)ethyl]-2-(4-nitrobenzamido)ethylamine;
N-Ethyl-N-[1-methyl-2-(3-thienyl)ethyl]-2-(4-nitrobenzenesulfonamido)ethylamine;
N-Ethyl-N-[2-methyl-2-(3-thienyl)ethyl]-2-(4-nitrobenzamido)ethylamine;
4-(4-Aminophenyl)-N-ethyl-N-[2-(3-thienyl)ethyl]butylamine;
4-(4-Aminophenyl)-N-ethyl-N-[1-methyl-2-(3-thienyl)ethyl]butylamine;
4-(4-Aminophenyl)-N-pentyl-N-[1-methyl-2-(3-thienyl)ethyl]butylamine;
2-(4-Aminobenzenesulfonamido)-N-ethyl-N-[1-methyl-2-(3-thienyl)ethyl]ethylamine;
2-(4-Aminobenzamido)-N-ethyl-N-[2-methyl-2-(3-thienyl)ethyl]ethylamine;
N-Ethyl-4-(4-methanesulfonylaminophenyl)-N-[2-[3-(2-thienyl)]propyl]butylamine;
N-Ethyl-4-(4-methanesulfonylaminophenyl)-N-[1-propyl-2-(2-thienyl)ethyl]butylamine;
N-Ethyl-4-(4-methanesulfonylaminophenyl)-N-[1-methyl-2-(3-thienyl)ethyl]butylamine;
N-Ethyl-4-(4-methanesulfonylaminophenyl)-N-[1-propyl-2-(3-thienyl)ethyl]butylamine;
N-Ethyl-2-(4-methanesulfonylaminophenoxy)-N-[1-methyl-2-(3-thienyl)ethyl]ethylamine;
N-Ethyl-3-(4-methanesulfonaminophenoxy)-N-[1-methyl-2-(3-thienyl)ethyl]propylamine;
N-Ethyl-2-(4-methanesulfonylaminobenzamido)-N-[1-methyl-2-(3-thienyl)ethyl]ethylamine; and
N-Ethyl-2-(4-methanesulfonylamidobenzenesulfonamido)-N-[1-methyl-2-(3-thienyl)ethyl]ethylamine.

5. The compound according to claim 1 selected from the group consisting of:
N-[1-Methyl-2-(3-thienyl)ethyl]-4-(4-nitrophenyl)butylamine;
N-Ethyl-N-[1-methyl-2-(3-thienyl)ethyl]-4-(4-nitrophenyl)butylamine;
N-Ethyl-N-[1-methyl-2-(3-thienyl)ethyl]-2-(4-nitrophenoxy)ethylamine;
N-Ethyl-N-[1-methyl-2-(3-thienyl)ethyl]-2-(4-nitrobenzamido)ethylamine;
N-Ethyl-N-[2-methyl-2-(3-thienyl)ethyl]-2-(4-nitrobenzamido)ethylamine;
N-Ethyl-4-(4-methanesulfonylaminophenyl)-N-[2-[3-(2-thienyl)]propyl]butylamine;
N-Ethyl-4-(4-methanesulfonylaminophenyl)-N-[1-methyl-2-(3-thienyl)ethyl]butylamine;
N-Ethyl-4-(4-methanesulfonylaminophenyl)-N-[1-propyl-2-(3-thienyl)ethyl]butylamine;
N-Ethyl-2-(4-methanesulfonylaminophenoxy)-N-[1-methyl-2-(3-thienyl)ethyl]ethylamine;
N-Ethyl-3-(4-methanesulfonaminophenoxy)-N-[1-methyl-2-(3-thienyl)ethyl]propylamine;
N-Ethyl-2-(4-methanesulfonylaminobenzamido)-N-[1-methyl-2-(3-thienyl)ethyl]ethylamine; and
N-Ethyl-2-(4-methanesulfonylamidobenzenesulfonamido)-N-[1-methyl-2-(3-thienyl)ethyl]ethylamine.

6. N-Ethyl-N-[1-methyl-2-(3-thienyl)ethyl]-4-(4-nitrophenyl)butylamine.

7. 2-(4-Methanesulfonylaminobenzamido)-N-ethyl-N-[1-methyl-2-(3-thienyl)-ethyl]ethylamine.

8. An antiarrhythmic pharmaceutical composition comprising one or more compounds according to claim 1 and a pharmaceutically inert carrier.

9. A method of increasing the effective refractory period in a mammal comprising administering an effective amount of a compound according to claim 1 to a mammal.

10. A method of increasing the effective refractory period in a mammal comprising administering an effective amount of a compound according to claim 2 to a mammal.

11. A method of increasing the effective refractory period in a mammal comprising administering an effective amount of a compound according to claim 4 to a mammal.

12. A method of increasing the effective refractory period in a mammal comprising administering an effective amount of a compound according to claim 5 to a mammal.

13. A method of increasing the effective refractory period in a mammal comprising administering an effective amount of a compound according to claim 6 to a mammal.

14. A method of increasing the effective refractory period in a mammal comprising administering an effective amount of a compound according to claim 7 to a mammal.

* * * * *